(12) United States Patent
Siravo et al.

(10) Patent No.: US 9,848,923 B2
(45) Date of Patent: Dec. 26, 2017

(54) LOCKING SYSTEM FOR ORTHOPEDIC IMPLANTS

(75) Inventors: Mark Siravo, East Norristown, PA (US); Glen Pierson, Glenmoore, PA (US); Charles West, Garnet Valley, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1896 days.

(21) Appl. No.: 12/843,421

(22) Filed: Jul. 26, 2010

(65) Prior Publication Data

US 2011/0178521 A1 Jul. 21, 2011

Related U.S. Application Data

(60) Provisional application No. 61/229,119, filed on Jul. 28, 2009.

(51) Int. Cl.
*A61B 17/56* (2006.01)
*A61B 17/58* (2006.01)
(Continued)

(52) U.S. Cl.
CPC ............ *A61B 17/725* (2013.01); *A61B 17/84* (2013.01); *A61B 17/92* (2013.01); *A61B 17/80* (2013.01); *A61B 2017/90* (2013.01)

(58) Field of Classification Search
CPC . A61B 17/72; A61B 17/7291; A61B 17/1725; A61B 17/7233; A61B 17/744; A61B 17/7241; A61B 17/725; A61B 17/8625; A61B 17/164; A61B 17/746; A61B 17/863; A61B 17/864; A61B 17/58; A61B 17/56; A61F 2/30
(Continued)

(56) References Cited

U.S. PATENT DOCUMENTS 5,129,906 A 7/1992 Ross et al.
5,246,441 A * 9/1993 Ross et al. ............ 606/53
(Continued)

OTHER PUBLICATIONS

Ring dictionary definition | ring defined (Ring dictionary definition | ring defined) http://www.yourdictionary.com/ring#american-heritage. Retrieved Dec. 16, 2014.*
(Continued)

*Primary Examiner* — Eduardo C Robert
*Assistant Examiner* — Michelle C Eckman
(74) *Attorney, Agent, or Firm* — Fay Kaplun & Marcin, LLP

(57) ABSTRACT

A locking tack for attaching a bone fixation device to a bone includes (a) an elongated body including a distal portion formed of a weldable material and sized to be received within a bore through a portion of a target bone and a proximal portion which, when the distal portion is in a desired position within a target bone, extends out of the bone; (b) a channel extending longitudinally through the elongated body from a proximal end thereof to a channel distal end within the distal portion of the elongated body; and (c) an engaging feature at a distal end of the channel configured to engage an extraction mechanism so that forces applied to the extraction mechanism are transmitted to the distal end of the elongated body.

7 Claims, 5 Drawing Sheets

(51) Int. Cl.
  *A61F 2/30* (2006.01)
  *A61B 17/72* (2006.01)
  *A61B 17/84* (2006.01)
  *A61B 17/92* (2006.01)
  *A61B 17/80* (2006.01)
  *A61B 17/90* (2006.01)

(58) Field of Classification Search
  USPC .................................... 606/62–68, 300–321
  See application file for complete search history.

(56) References Cited

U.S. PATENT DOCUMENTS

| | | | | |
|---|---|---|---|---|
| 5,716,358 | A * | 2/1998 | Ochoa et al. | 606/62 |
| 5,741,282 | A * | 4/1998 | Anspach et al. | 606/151 |
| 5,840,078 | A * | 11/1998 | Yerys | 606/151 |
| 5,971,985 | A * | 10/1999 | Carchidi et al. | 606/312 |
| 6,290,701 | B1 * | 9/2001 | Enayati | 606/327 |
| 6,575,976 | B2 * | 6/2003 | Grafton | 606/916 |
| 6,582,453 | B1 * | 6/2003 | Tran et al. | 606/232 |
| 6,747,121 | B2 * | 6/2004 | Gogolewski | 528/354 |
| 7,033,365 | B2 * | 4/2006 | Powell et al. | 606/99 |
| 7,608,062 | B2 * | 10/2009 | Sweeney | 604/264 |
| 7,771,428 | B2 * | 8/2010 | Siravo et al. | 606/62 |
| 7,896,907 | B2 * | 3/2011 | McDevitt et al. | 606/304 |
| 2005/0015061 | A1 * | 1/2005 | Sweeney | 604/264 |
| 2005/0065525 | A1 * | 3/2005 | Aringskog et al. | 606/72 |
| 2005/0273102 | A1 * | 12/2005 | Powell et al. | 606/62 |
| 2005/0277936 | A1 * | 12/2005 | Siravo et al. | 606/62 |
| 2005/0277940 | A1 * | 12/2005 | Neff | 606/73 |
| 2006/0235410 | A1 | 10/2006 | Ralph et al. | |
| 2006/0241593 | A1 * | 10/2006 | Sherman et al. | 606/61 |
| 2007/0010818 | A1 | 1/2007 | Stone et al. | |
| 2008/0021474 | A1 * | 1/2008 | Bonutti et al. | 606/64 |
| 2008/0228186 | A1 * | 9/2008 | Gall et al. | 606/63 |
| 2009/0171396 | A1 * | 7/2009 | Baynham et al. | 606/280 |
| 2010/0076437 | A1 * | 3/2010 | Tilson et al. | 606/63 |
| 2010/0114097 | A1 * | 5/2010 | Siravo et al. | 606/62 |
| 2010/0217329 | A1 * | 8/2010 | Brown et al. | 606/301 |
| 2010/0249838 | A1 * | 9/2010 | Stopek et al. | 606/246 |
| 2010/0268229 | A1 * | 10/2010 | Siravo et al. | 606/64 |

OTHER PUBLICATIONS

Ring (The Free Dictionary) http://www.thefreedictionary.com/ring. Retrieved Dec. 16, 2014.*

* cited by examiner

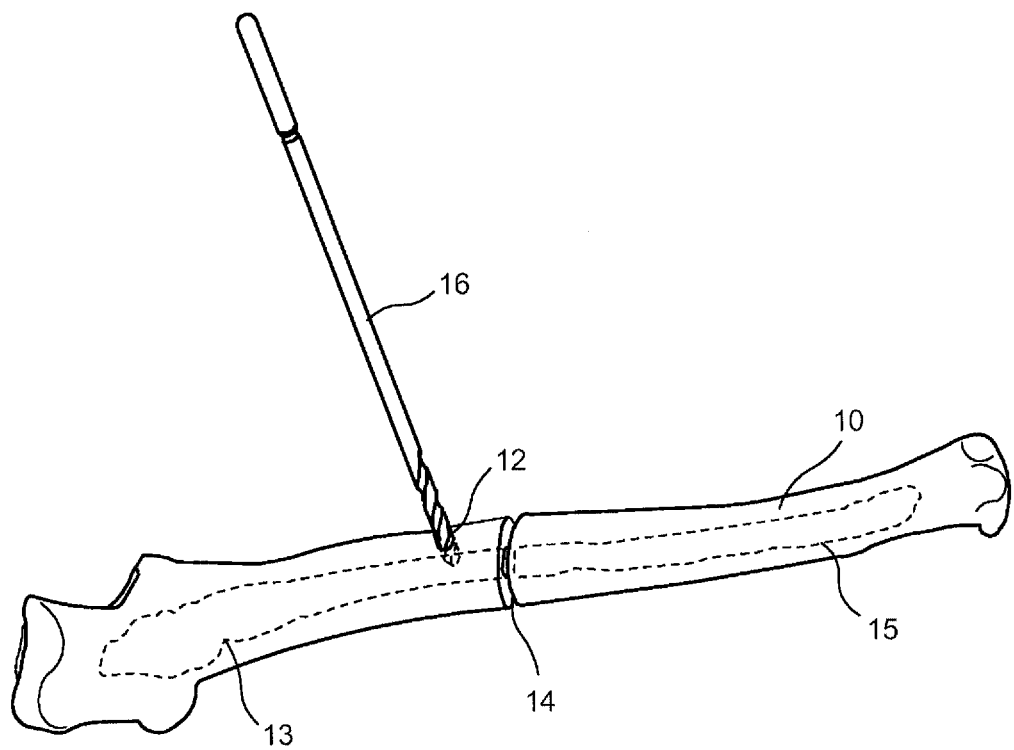
F I G. 3
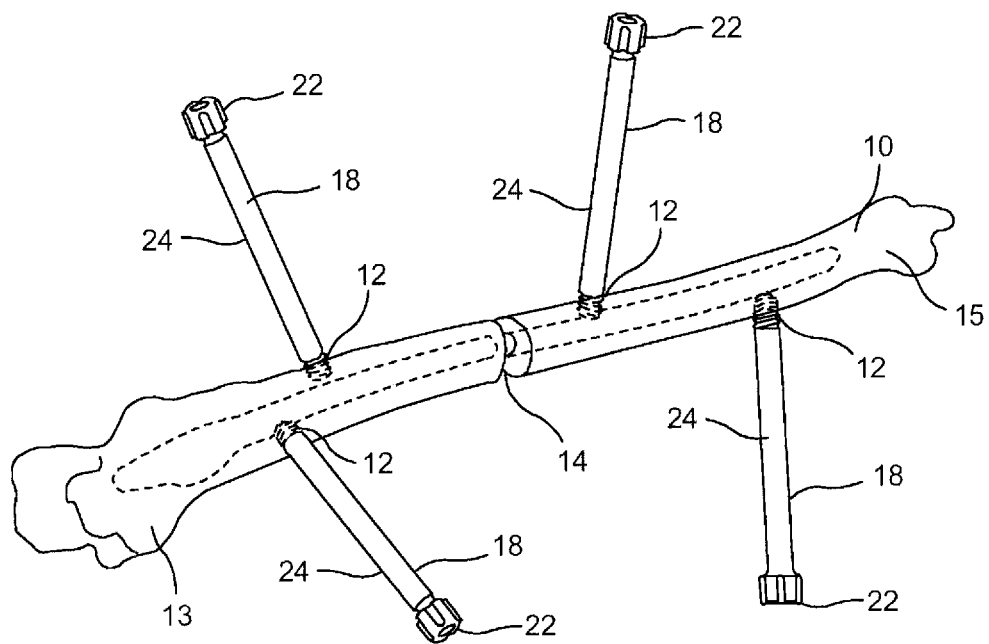
F I G. 4

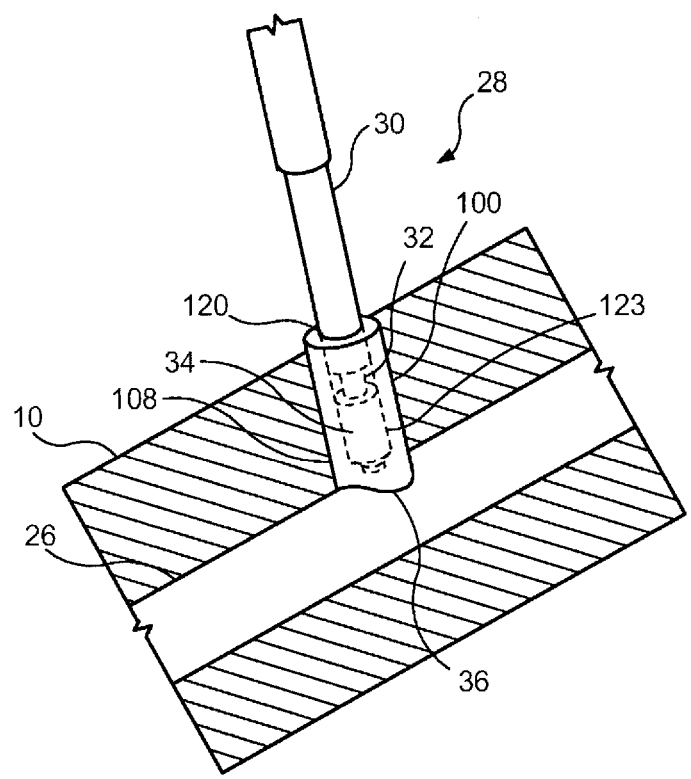
F I G. 5

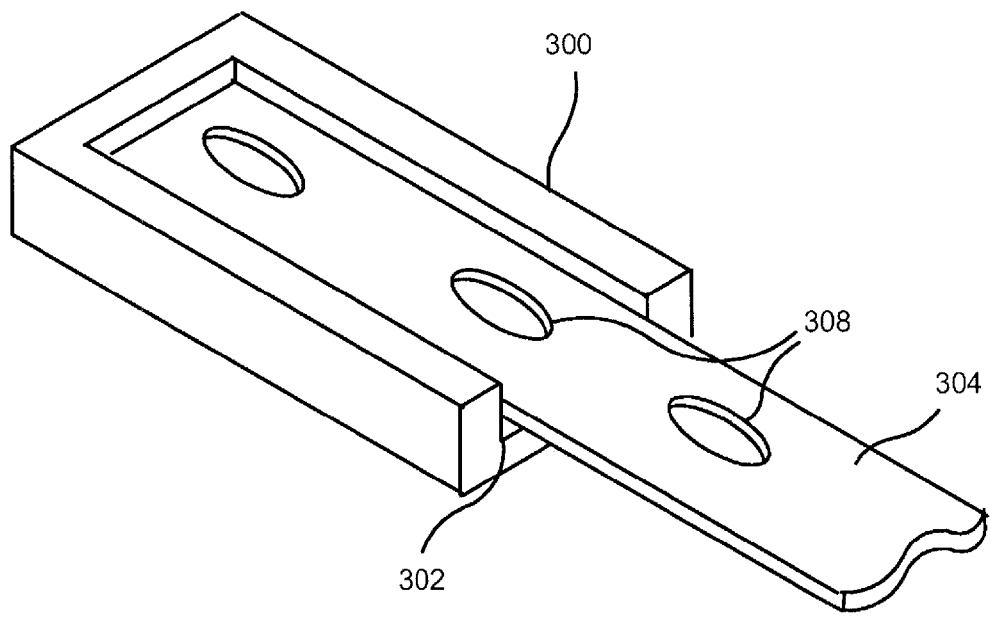
F I G. 8
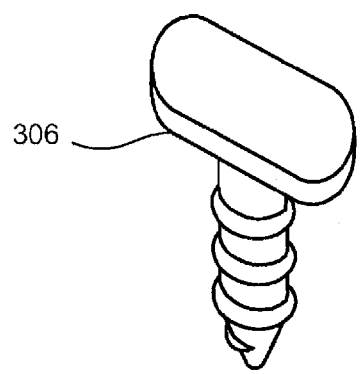
F I G. 9

LOCKING SYSTEM FOR ORTHOPEDIC IMPLANTS

PRIORITY CLAIM

The present application claims priority to U.S. Provisional Application Ser. No. 61/229,119 entitled "Locking System for Orthopedic Implants" filed on Jul. 28, 2009 to Mark Siravo, Glen Pierson and Charles West, the entire disclosure of which is incorporated herein by reference.

FIELD OF THE INVENTION

The present application relates to the field of bone fixation and, more specifically, to a system and method for the fixation of bone fractures by attaching a bone implant to a bone fixation apparatus.

BACKGROUND

Procedures for the fixation and stabilization of bones commonly employ nails inserted into the medullary canal. Such procedures often use metallic implants that rely on cross-locking elements situated on proximal and distal ends of the nails. The cross-locking elements are positioned on proximal and distal ends of the nails to avoid stress risers that might result if they were located along a middle portion thereof. This concept, although effective in long bones (e.g., the femur, the tibia) does not provide adequate torsional stability when positioned in smaller bones (e.g., the ulna, the radius). Alternate designs employed in the art rely on a frictional engagement between the nail and the intramedullary canal to provide stability. However, the frictional force relies heavily on a fit between the nail and the intramedullary canal as well as a rigidity of the bone itself and thus does not provide a consistent frictional engagement due to variations in human anatomy.

Furthermore, implantation of the nails in areas of the body that are subjected to increased cantilever being forces (e.g., lateral plating of the proximal humerus) often results in the nail losing bony purchase in osteoporotic bone. Presently available bone fixation devices employ multiple screws that are inserted at various angles into the bone to increase a surface contact area between the bone fixation device and the bone. However, if a bone fixation device needs to be repositioned within the bone, the voids created by the screws increase the susceptibility of the bone to further fracture. Furthermore, the placement of multiple screws in the bone proves to be challenging in that it is difficult to ensure proper anatomical fixation prior to the insertion of locking screws into the bone fixation device.

SUMMARY OF THE INVENTION

The present invention relates to a bone implant system for attaching a bone fixation device to a bone. The system comprises a locking tack having an elongated body including a distal portion formed of a weldable polymeric material and sized to be received within a bore through a portion of a target bone and a proximal portion which, when the distal portion is in a desired position within a target bone, extends out of the bone. The bone implant system also comprises a channel extending longitudinally through the elongated body from a proximal end thereof to a channel distal end within the distal portion of the elongated body, and an engaging feature at a distal end of the channel configured to engage an extraction mechanism so that forces applied to the extraction mechanism are transmitted to the distal end of the elongated body. Components of the bone implant system may be welded together by melting the polymeric material of the locking tack thereover. An extraction mechanism may be used to extract the welded locking tack from a bone fixation device to which it is welded.

BRIEF DESCRIPTION OF THE DRAWINGS

FIG. 3 shows a perspective view of the bone being pre-drilled in accordance with a first exemplary step of a method according to the present invention;

FIG. 4 shows a perspective view of a second exemplary step of a method according to the present invention wherein tack locators are inserted into the bone;

FIG. 5 shows a perspective view of a third exemplary step of a method according to the present invention wherein the locking tack of FIG. 1 is being extracted from the bone;

FIG. 8 shows a bone plate sleeve according to another embodiment of the present invention; and FIG. 9 shows a bone locking tack for use with the bone plate sleeve of FIG. 8.

DETAILED DESCRIPTION

The present invention relates to a system and method for the fixation of bones in living bodies. Specifically, the present invention is directed to a system including tack locators configured for insertion into holes drilled in a bone at locations selected for the bonding of locking tacks to an intramedullary nail. The tack locators are securely inserted into the holes to prevent their being dislodged during manipulation of the bone portions prior to the insertion of the intramedullary nail into the medullary canal and to prevent insertion of the tack locators into the medullary canal where they could interfere with the insertion of the medullary nail. After an intramedullary nail has been inserted to a desired position within the medullary canal, the tack locators are removed and novel locking tacks are inserted into the holes until they contact the nail. The locking tacks are then bonded to the nail and cut off flush to the surface of the bone. Distal portions of the locking tacks according to the present invention (i.e., portions remaining within the cortex of the bone after the tacks have been cut off) further include structures facilitating their removal. Specifically, a locking tack according to the invention includes a feature formed within a distal end thereof adapted to mate with a driving tool so that rotation of the tool torques the locking tack until the bond with the medullary nail is broken. Specifically, the distal portion of the locking tack is provided with a structure formed as a threaded cannula so that insertion of an extraction mechanism into the threaded cannula exerts a concentrated stress at the weld joint to ensure complete separation of the locking tack from the medullary nail.

As described in more detail below, a locking tack according to the present invention comprises an elongated body having a proximal portion, a distal portion and an increased diameter ring provided over the elongated body. A cannula extends a predetermined distance into the locking tack from the proximal end of the tack. A distal end of the cannula positioned within a portion of the locking tack which will remain within the cortex of the bone after the tack is cut off flush to bone includes a feature adapted to engage a shaped tip of an extraction mechanism. The locking tack is formed of a material permitting ultrasound welding or mechanical welding (e.g., implantable polymers and metals). It is noted that although the present invention is described with respect to particular bones of the body, the device may be employed in any bone without deviating from the spirit and scope of the present invention. As used in this application, the term proximal refers to a direction approaching a physician or other user of the device and the term distal refers to a direction along the device away from the user. In an operative configuration, the distal end of the device is received within the bone while the proximal end remains external to the bone.

Figure 2:
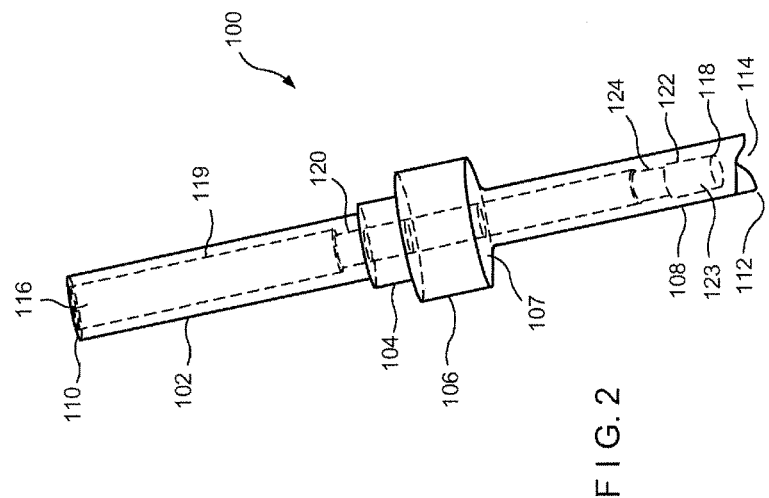
FIG. 2 shows a semi-transparent view of the locking tack of FIG. 1.
Figure 1:
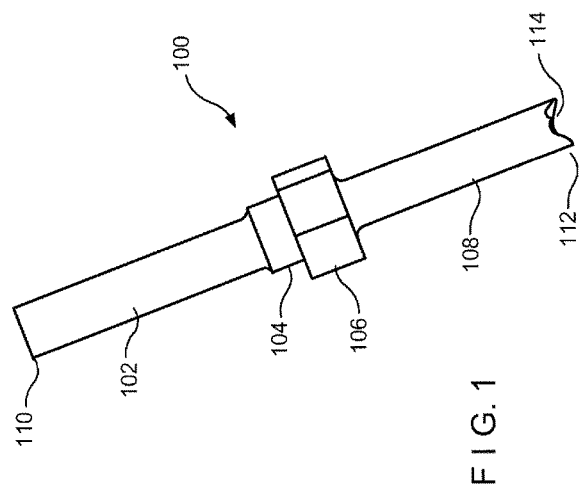
FIG. 1 shows a perspective view of a locking tack according to a first embodiment of the present invention.

FIG. 1 shows a first exemplary locking tack 100 according to the present invention. The locking tack 100 is formed as an elongated substantially cylindrical element comprising a proximal portion 102, a first ring 104, a second ring 106 and a distal portion 108. The first and second rings 104, 106 are configured to mate with correspondingly shaped elements (not shown) of a driving mechanism (not shown) used to weld the locking tack 100 in the bone. The proximal portion 102 extends from a proximal end 110 to the first ring 104 which has a diameter greater than that of the proximal portion 102. A second ring 106 immediately distal to the first ring 104 has a diameter greater than that of the first ring 104 and forms a distally facing abutting surface 107 which defines a maximum extent to which the locking tack 100 may be inserted into the bone as will be described below. The length of the distal portion 108 is preferably selected to be substantially equal to a thickness of the cortex of the bone plus a desired depth of penetration of the distal portion 108 into the medullary canal. The diameter of the distal portion 108 extending from the abutting surface 107 to a distal end 112 of the locking tack 100 has a diameter selected to be substantially equivalent to the diameter of a hole in the bone within which it is to reside. In this embodiment, the diameter of the distal portion 108 is substantially equal to that of the proximal portion 102. However, as would be understood by those skilled in the art, this is not necessary. The distal end 112 of the locking tack 100 includes an arced cut 114 extending therethrough to define a non-planar end face selected to substantially match a profile of a portion of the outer surface of the intramedullary nail to which it is to be bonded. The locking tack 100 of the present invention may be formed of a polymer, metal or any other suitable biocompatible weldable material. Alternatively, the distal portion 108 may be formed of a suitable weldable material which the proximal portions which will not be welded and which will be withdrawn from the body may be formed of other materials.

A cannula 116 extends into the locking tack 100 from the proximal end 110 to a cannula distal end 118 within the distal portion 108 a predetermined distance from the distal end 112. The cannula 116 includes a proximal cannula portion 119 with a first diameter, a medial cannula portion 120 having a second diameter smaller than the first diameter and a distal cannula portion 122 housing an insert 123. The insert 123 is formed of a substantially rigid material capable of exerting a torque on the locking tack 100 sufficient to cause disengagement from a bone fixation device to which it has been welded, as will be described in greater detail in the exemplary method of the present invention. The insert 123 is sized so that, when inserted into the target bone, the entire insert 123 is located within the bone and remains therein after the locking tack 100 has been cut to lie flush against an outer periphery of the bone. A proximal end of the insert comprises a hexagonal recess (not shown) to permit engagement with an exemplary extraction mechanism 28. The insert 123 is formed as a threaded element inserted into the cannula 116, for example, during manufacturing and adapted to engage the extraction mechanism 28. For example, the insert 123 includes a proximal end shaped to lockingly engage the extraction mechanism 28 including, for example, a threaded proximal end which may be screwed onto a correspondingly threaded distal end of the extraction mechanism 28. As described in more detail below, when it is desired to remove a previously inserted locking tack 100, the extraction mechanism 28 is inserted into the portion of the cannula 116 extending through the remaining portion of the locking tack 100 (i.e., the distal portion 108) until it lockingly engages the insert 123. As would be understood by those skilled in the art, at this point, the locking engagement of the extraction mechanism 28 and the insert 123 requires only that they be non-rotatably coupled to one another. Torque applied to the extraction mechanism 28 is transmitted the distal portion 108 of the locking tack until the bond between the locking tack 100 and the intramedullary nail shears and the locking tack 100 is freed from the intramedullary nail. At this point, the threaded engagement of the extraction mechanism 28 and the insert 123 allows a user to withdraw the locking tack 100 from the body by simply withdrawing the extraction mechanism 28. When all of the locking tacks 100 bonded to the intramedullary nail have been withdrawn along with any other elements locking the nail within the medullary canal, the nail may be withdrawn in the same manner as in conventional removal procedures. Those skilled in the art will recognize that, alternatively, a separate locking feature may be formed within the portion of the cannula 116 extending within the distal portion 108 to couple the extraction mechanism 28 to the distal portion 108 of the locking tack 100 so that the distal portion 108 is withdrawn with the extraction mechanism 28. For example, the insert 123 may comprise a cannula extending therethrough wherein the cannula is shaped and sized to engage a distal tip of a flathead screwdriver. A distal portion of the flathead screwdriver may be tapered to prevent inadvertent withdrawal thereof from the insert 123.

Specifically, as will be described in greater detail with respect to the exemplary method of the present invention, the exemplary extraction mechanism 28 for use with the locking tack 100 of the present invention comprises a driver tip 30 having an elongated, substantially cylindrical body. A distal end of the driver tip 30 comprises a flange 32 connected to an increased diameter portion 34, the increased diameter portion 34 being formed with threads sized to threadably engage the insert 123 when inserted into the cannula 116. The cannula 116 further comprises a flanged recess 124 with a substantially concave shape, the flanged recess 124 being dimensioned to engage the flange 32 while still permitting insertion of the increased diameter portion 34 of the driver tip 30 therepast.

FIGS. 3-5 depict an exemplary method according to the present invention for inserting a locking tack 100 through a hole 12 previously drilled in a bone 10 to bond the locking tack 100 to an insert within the bone 10 (e.g., an intramedullary nail 26). In this example the bone 10 includes a fracture 14 separating the bone 10 into first and second fragments 13, 15, respectively. As shown in FIGS. 3 and 4, a drill 16 is used to drill bores 12 into each of the first and second bone fragments 13, 15 at locations at which it is desired to bond locking tacks to the insert. As those skilled in the art will understand, each of the first and second bone fragments 13, 15 may be provided with multiple bores 12 depending on the desired number and location of locking tacks 100. After the bores 12 have been drilled into the bone 10, a distal end of a tack locator 18 is inserted into each bore 12 and, preferably, engaged with the bone 10 in a manner to prevent the tack locator 18 from becoming inadvertently disengaged from the bone 10. Each of the tack locators 18 comprises an elongated shaft 24 connected to an increased diameter head 22 at a proximal end thereof. The diameter of a distal end of the shaft 24 is selected to permit frictional engagement with the bore 12, as would be understood by those of skill in the art. Furthermore, at least a distal portion of each shaft 24 is threaded to permit a screw-like engagement with an inner surface of the bore 12 to ensure frictional engagement with the bone and minimize the chance that the tack locators 18 will be inserted into the bone 10 beyond a desired depth and/or that they will be inadvertently dislodged from the bone 10. The threading formed on the tack locators 18 is tapered to prevent insertion beyond the desired depth. Specifically, an outer diameter of the tack locator 18 tapers to a smaller diameter toward a distal end thereof so that, as the tack locator 18 is screwed into the bone 10, the increase in diameter of the shaft 24 prevents insertion of the tack locator into the bone 10 beyond the desired depth. A length of the tack locator 18 is selected so that, when the distal end thereof is inserted to a desired depth within a bore 12 in the bone 10, the proximal extends out of the bone 10 by a distance sufficient that the proximal end and the head 22 remain accessible outside the body. This facilitates location and manipulation of the first and second bone fragments 13, 15 to achieve a desired spatial orientation of the portions of the bone 10 relative to one another.

In a subsequent step, the first and second bone fragments 13, 15 are properly aligned to a corrective position and the intramedullary nail 26 is inserted into the medullary canal in accordance with procedures known in the art. Once the intramedullary nail 26 has been inserted to a target location in the medullary canal, the tack locators 18 are removed from the bores 12 and locking tacks 100 are inserted into each of the bores 12. Specifically, the distal portions 108 of the locking tacks 100 which have outer diameters substantially equivalent to inner diameters of the bores 12 are freely movable within the bores 12. The locking tacks 100 are inserted into each of the bores 12 until distal ends 112 thereof come into contact with the intramedullary nail 26. A driving mechanism (not shown) then engages the locking tack 100 and applies energy thereto in a known manner to weld the distal portion 108 of each tack 100 to the outer surface of the intramedullary nail 26. The driving mechanism (not shown) may, for example, comprise a force sensor configured to ensure that a correct load is applied to the intramedullary nail 26 via the locking tack 100 during welding. Specifically, the force sensor may monitor the force and produce a warning when the applied force is lower than a minimal required force or greater than a maximum force to be applied to ensure that the load being applied falls is maintained within a desired range. According to a preferred method, the driving mechanism (not shown) corrects the load applied while the locking tack 100 is pressed against the intramedullary nail 26. Those skilled in the art will understand that the simultaneous performance of these steps prevents the exertion of an extraneous welding force to the locking tack 100. The locking tacks 100 are inserted into each of the first and second bone fragments 13, 15 in succession such that, once all locking tacks 100 within the first bone fragment 13 at a first end of the bone 10 have been welded, an instrument or end cap may be inserted into the second bone fragment 15 located at an opposing end of the bone 10, allowing the second unwelded bone fragment 15 to slide along the intramedullary nail 26 until the bone 10 is properly aligned. Locking tacks 100 in the second bone fragment 15 may then be welded to lock the intramedullary nail 26 to the bone 10 in the same manner as the tacks 100 were welded to the portions of the nail 26 within the first bone fragment 13. Once all of the locking tacks 100 have been welded in place, a cutting device (not shown) known in the art is used to cut the exposed portions of the locking tack 100 flush against an outer periphery of the bone 10.

When it is necessary to remove an intramedullary nail 26 implanted using locking tacks 100 according to the invention, the locations of the portions of the locking tacks 100 remaining in the bone are exposed (i.e., through surgical incisions) and the extraction mechanism 28 discussed earlier is inserted into the distal portion of the cannula 116 and engaged with the insert 123. Specifically, the driver tip 30 of the extraction mechanism 28 is inserted into the medial cannula portion 120 until the increased diameter portion 34 threadably engages the insert 123 temporarily locking the extraction mechanism 28 to the locking tack 100. After the increased diameter portion 34 has been positioned as desired within the insert 123, the extraction mechanism 28 may be rotated to drive the insert 123 toward the joint 36 and exert torque thereon until the joint 36 has separated. Alternatively, the extraction mechanism 28 may be angled back and forth about a longitudinal axis of the locking tack 100 to fatigue the joint 36 until the joint 36 is severed. As the threading couples the locking tack 100 to the extraction mechanism 28, as the extraction mechanism 28 is withdrawn from the body, the locking tack 100 is removed with it. The locking tack 100 may be decoupled from the extraction mechanism 28 and the process may be repeated until all of the locking tacks 100 have been detached from the intramedullary nail 26. At this point, the intramedullary nail may be removed in a conventional manner as would be understood by those skilled in the art.

Figure 6:
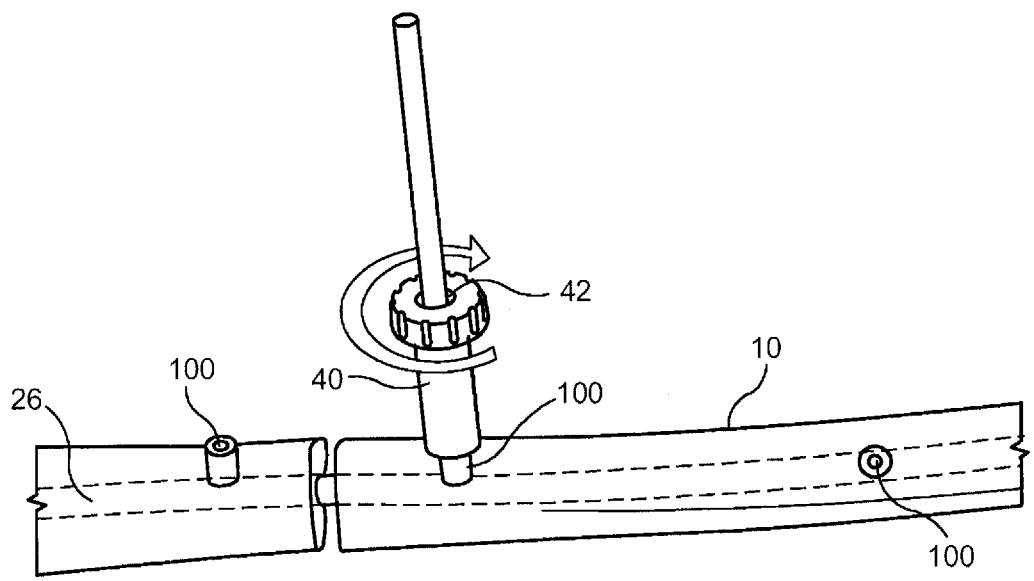
FIG. 6 shows a perspective view of a stop facilitating extraction of the locking tack of FIG. 1.

FIG. 6 depicts another embodiment of the present invention wherein a threaded stop 40 may be used to aid in extraction of the locking tack from the bone 10. The stop 40 is formed as a hollow cylindrical element with a threaded channel 42 extending longitudinally therethrough, a diameter of the channel 42 being substantially equivalent to an outer diameter of the driver tip 30. A direction of the threading formed along the channel 42 is opposite a direction of threading formed on an outer wall of the driver tip 30. The stop 40 may also be provided with an increased diameter head 44 having a torx shape, the head 44 aiding a manual screwing of the stop 40 over the driver tip 30. Specifically, after insertion of the driver tip 30 into the cannula 116 as detailed earlier, the stop 40 is threaded down the driver tip 30 to an outer cortex of the bone 10. Once the stop 40 has assumed a position contacting an outer periphery of the bone 10, the stop 40 is held in place while the driver tip 30 is screwed subsequently deeper into the bone 10 until the joint 36 is severed.

Figure 7:
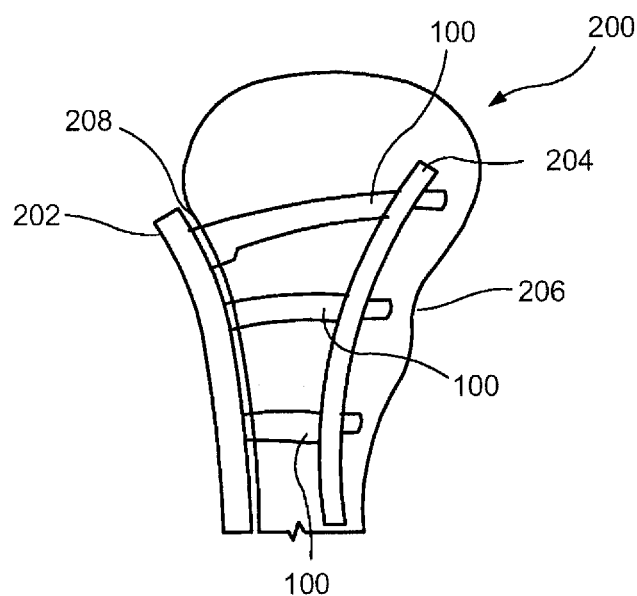
FIG. 7 shows a partial cross-sectional view of a second exemplary embodiment of the present invention wherein an exemplary locking tack is bonded to an extramedullary plate.

FIG. 7 depicts another alternate embodiment of the present invention, wherein the locking tacks 100 are used to connect a bone plate 202 to a bone fixation device such as an intramedullary plate 204 or intramedullary nail implanted within a bone 206. As would be understood by those skilled in the art, the bone plate 202 and/or the intramedullary plate 204 may be formed of a metal or polymer depending on the desired characteristics of these components. In accordance with an exemplary method for the system 200 of FIG. 6, the intramedullary plate 204 is inserted into the bone to a desired position. The plate 202 is then positioned correspondingly on the outer surface of the bone and bores 208 are drilled through the bone and the intramedullary plate 204 in positions corresponding to the holes in the plate 202. The locking tacks 100 are then inserted through the bone plate 202, into the bores 208 and through the holes which were drilled through the intramedullary plate 204. Once the locking tacks 100 are in target positions within the bores 208, welding energy is applied thereto to lock the locking tacks 100 against the bone plate 202 and the intramedullary plate 204. If intramedullary fixation is not desired, bone screws may be employed in place of the locking tacks.

FIGS. 8-9 depict another embodiment of the present invention wherein a sleeve 300 or alignment member may be provisionally locked to a bone (not shown) prior to definitive fixation. Specifically, the sleeve 300 is formed as a substantially rectangular element having a recess 302 dimensioned to permit slidable insertion of at least a portion of a bone plate 304 therein. The recess 302 may be shaped so that, when the bone plate 304 is inserted therein, the bone plate 304 assumes a desired placement angle. In accordance with an exemplary method for the system of FIG. 8, locking tacks 306 are first inserted into bores drilled into the bone (not shown) and cut flush against an outer surface of the bone. The sleeve 300 is inserted over the bone plate 304 and the bone fragments are properly aligned. The bone locking tacks 306 are then welded to the sleeve 300 using ultrasonic welding for provisional fixation. Bone screws (not shown) may then be inserted through plate holes 308 of the bone plate 304 for definite fixation thereof. Once the bone plate has been properly positioned, the sleeve or alignment member may be removed. The locking tacks 300 may then be removed in the same manner described above in conjunction with the extraction mechanism 28.

Although the present invention has been described with reference to preferred embodiments, it is submitted that various modifications can be made to the exemplary system and method without departing from the spirit and scope of the invention.

What is claimed is:

1. A locking tack for attaching a bone fixation device to a bone, comprising:
   an elongated body including a distal portion formed of a weldable material and sized to be received within a bore through a portion of a target bone such that the distal portion is configured to be welded to a bone fixation device inserted in the bone and a proximal portion which, when the distal portion is within the target bone, extends out of the bone;
   a channel extending longitudinally through the elongated body from a proximal end thereof to a channel distal end within the distal portion of the elongated body; and
   an engaging feature at a distal end of the channel configured to engage an extraction mechanism so that forces applied to the extraction mechanism are transmitted to the distal end of the elongated body to break a weld between the distal portion of the elongated body and the bone fixation device and remove the locking tack from the bone.

2. The locking tack of claim 1, further comprising a ring extending around the elongated body at a proximal end of the distal portion, the ring having a diameter greater than a diameter of the distal portion, the ring being sized and shaped to mate with a welding mechanism.

3. The locking tack of claim 1, wherein the engaging feature includes a first feature configured to non-rotatably couple the locking tack to an extraction mechanism and a second feature configured to longitudinally couple the locking tack to an extraction mechanism, the second feature including a threading on a wall of the channel sized and positioned to engage a corresponding threading on a distal surface of an extraction mechanism.

4. The locking tack of claim 1, wherein the engagement feature is formed as an insert permanently mounted within the channel.

5. The locking tack of claim 1, wherein the distal portion of the elongated member is formed of one of a polymer and a metal.

6. The locking tack of claim 1, wherein the distal end of the elongated member is shaped to correspond to a shape of a bone implant to which the locking tack is to be coupled.

7. The locking tack of claim 1, wherein the elongated body is formed of a weldable polymer.

\* \* \* \* \*